US008317714B2

(12) United States Patent
Hendriks et al.

(10) Patent No.: US 8,317,714 B2
(45) Date of Patent: Nov. 27, 2012

(54) SYSTEMS AND METHODS FOR CAPTURE AND DISPLAY OF BLOOD PRESSURE AND ULTRASOUND DATA

(75) Inventors: Randall Albert Hendriks, Toronto (CA); Desmond Hirson, Thornhill (CA); Christopher Scott Rabuka, Ajax (CA)

(73) Assignee: VisualSonics Inc., Toronto (CA)

( * ) Notice: Subject to any disclaimer, the term of this patent is extended or adjusted under 35 U.S.C. 154(b) by 1663 days.

(21) Appl. No.: 11/507,068

(22) Filed: Aug. 18, 2006

(65) Prior Publication Data
US 2007/0066898 A1   Mar. 22, 2007

Related U.S. Application Data

(60) Provisional application No. 60/709,837, filed on Aug. 19, 2005.

(51) Int. Cl.
*A61B 5/02* (2006.01)
*A61B 8/00* (2006.01)

(52) U.S. Cl. ........ 600/485; 600/504; 600/440; 600/441; 600/443; 600/453; 600/454

(58) Field of Classification Search .................. 600/481, 600/483, 485, 490–504, 440, 441, 443, 453, 600/454
See application file for complete search history.

(56) References Cited

U.S. PATENT DOCUMENTS

| | | | |
|---|---|---|---|
| 3,902,476 A * | 9/1975 | Hileman | ........................ 600/440 |
| 5,450,850 A | 9/1995 | Iinuma | |
| 6,090,047 A | 7/2000 | Kass et al. | |
| 6,436,043 B2 * | 8/2002 | Bonnefous | .................... 600/438 |
| 6,612,989 B1 | 9/2003 | Brock-Fisher | |
| 6,673,020 B2 | 1/2004 | Okada et al. | |
| 6,705,992 B2 | 3/2004 | Gatze | |
| 6,730,032 B2 | 5/2004 | Yamauchi | |
| 2002/0007119 A1 | 1/2002 | Pelissier | |
| 2003/0195409 A1 | 10/2003 | Seitz et al. | |
| 2004/0059220 A1 | 3/2004 | Mourad et al. | |
| 2004/0176678 A1 | 9/2004 | Murphy et al. | |
| 2004/0176689 A1 | 9/2004 | Yamauchi | |

(Continued)

FOREIGN PATENT DOCUMENTS
CN      85201969 U      4/1986

(Continued)

OTHER PUBLICATIONS

Extended European Search Report, European Patent Application No. EP 06813602.7, Dec. 6, 2010, 9 pages.

(Continued)

*Primary Examiner* — Navin Natnithithadha

(57) ABSTRACT

An ultrasonic imaging system comprises a processing system and an ultrasound imaging probe that is configured to transmit ultrasound energy into a selected portion of a subject and to receive echoes therefrom and to transmit data signals representative thereof to the processing system. The system further comprises a blood pressure sensor that is configured to measure the blood pressure of the subject and to transmit data signals representative thereof to the processing system. The processing system can processes the received ultrasound data signals to generate an ultrasound image and the received blood pressure data signals to generate a blood pressure trace. The processing system can also display the ultrasound image and blood pressure trace in a display image in which portions of the ultrasound image are displayed in temporal synchrony with portions of the blood pressure trace.

38 Claims, 12 Drawing Sheets

U.S. PATENT DOCUMENTS

| | | | |
|---|---|---|---|
| 2005/0015009 A1 | 1/2005 | Mourad et al. | |
| 2005/0143640 A1 | 6/2005 | Hoctor et al. | |
| 2006/0058660 A1* | 3/2006 | Sandy et al. | 600/437 |
| 2006/0058662 A1* | 3/2006 | Kobayashi et al. | 600/437 |
| 2006/0241463 A1* | 10/2006 | Shau et al. | 600/455 |

FOREIGN PATENT DOCUMENTS

| | | |
|---|---|---|
| CN | 2071055 U | 2/1991 |
| EP | 1123687 A2 | 8/2001 |
| JP | 05337110 A | 12/1993 |
| JP | 2001218768 A | 8/2001 |
| JP | 2001299752 A | 10/2001 |
| JP | 2002330968 A | 11/2002 |
| JP | 2004041605 A | 2/2004 |
| JP | 2005095675 A | 4/2005 |
| JP | 2005532097 A | 10/2005 |
| JP | 2006505294 A | 2/2006 |
| TW | 227665 B | 2/2005 |
| WO | WO-2004099814 A1 | 11/2004 |
| WO | WO 2007/022505 A2 | 2/2007 |

OTHER PUBLICATIONS

Office Action issued in China Patent Application No. 200680038226. 4, Oct. 23, 2009, 16 pages.

Office Action issued in China Patent Application No. 200680038226. 4, Jan. 12, 2011, 10 pages.

Foex P. and Leone BJ, "Pressure-volume loops: a dynamic approach to the assessment of ventricular function." J Cardiothorac Vasc Anesth. Feb. 1994;8(1):84-96.

Caputo, M., et al., "Assessment of myocardial performance with ventricular pressure-volume relations: clinical applications in cardiac surgery." Ital Heart J. Apr. 2000;1(4):269-274.

Sasayama S., et al., "Assessment of cardiac function by left heart catheterization: an analysis of left ventricular pressure-volume (length) loops." J Cardiogr Suppl. 1984;(1):25-34.

Boutouyrie, P., et al., "Increased carotid wall stress in vascular Ehlers-Danlos syndrome." Circulation 2004;109:1530-1535.

Bussy, C., et al., "Intrinsic stiffness of the carotid arterial wall material in essential hypertensives." Hypertension 2000;35:1049-1054.

Office Action issued in Japan Application No. 2008-527209, Aug. 19, 2011, 8 pages.

* cited by examiner

SYSTEMS AND METHODS FOR CAPTURE AND DISPLAY OF BLOOD PRESSURE AND ULTRASOUND DATA

CROSS-REFERENCE TO RELATED APPLICATIONS

This application claims the benefit of U.S. Provisional Application No. 60/709,837, filed on Aug. 19, 2005, which is herein incorporated by reference in its entirety.

BACKGROUND OF THE INVENTION

Assessment of myocardial performance, function and contractility is critically important for the evaluation of many patients with known or suspected heart disease. There has been growing interest in the dynamic assessment of cardiac contraction relying on the instantaneous relationships between pressure and dimensions in both the left and right ventricles.

Pressure-volume or pressure-dimension loops provide visual and parametric information regarding the performance of the right and left ventricle as a pump and help identify the pathophysiology of cardiac dysfunction and the extent of cardiac impairment. Moreover, these loops allow for determination and quantification of the success of many therapeutic interventions. Thus, accurate and efficient analysis of pressure and dimension relationships in the heart of patients and in clinical research using small animal subjects is critically important for assessing disease, response to therapeutics, and for developing new therapeutics and strategies for treating human and animal patients.

Current methods in the art for assessing pressure-volume or pressure-dimension relationships, including traditional echocardiography and conductance methods, can be overly complicated, time consuming and unreliable. Needed in the art are systems and methods for capture and display of blood pressure and ultrasound data.

SUMMARY OF THE INVENTION

A method for the capture and display of ultrasound data and blood pressure data from a subject comprises capturing ultrasound data and blood pressure data from the subject. The captured ultrasound and blood pressure data can be timestamped. The time-stamped ultrasound data and the time-stamped blood pressure data can be processed for display on a display device and the processed data can be displayed synchronously on the display device.

A system for the capture and display of ultrasound data and blood pressure data from a subject can comprise an ultrasonic transducer capable of transmitting ultrasound into the subject and of receiving echo data from the subject. The system can further comprise a blood pressure receiving mechanism capable of collecting blood pressure data from the subject and a processing system for receiving the echo data and the collected blood pressure data. The processing system can be further used to identify the received data with a time-stamp, and to display synchronously the time-stamped ultrasound and blood pressure data on a display device.

Other systems, methods, and aspects and advantages of the invention will be discussed with reference to the Figures and to the detailed description.

BRIEF DESCRIPTION OF THE DRAWINGS

The invention will be described by way of example, in the detailed description, with particular reference to the accompanying Figures in which.

DETAILED DESCRIPTION OF THE INVENTION

Figure 1:
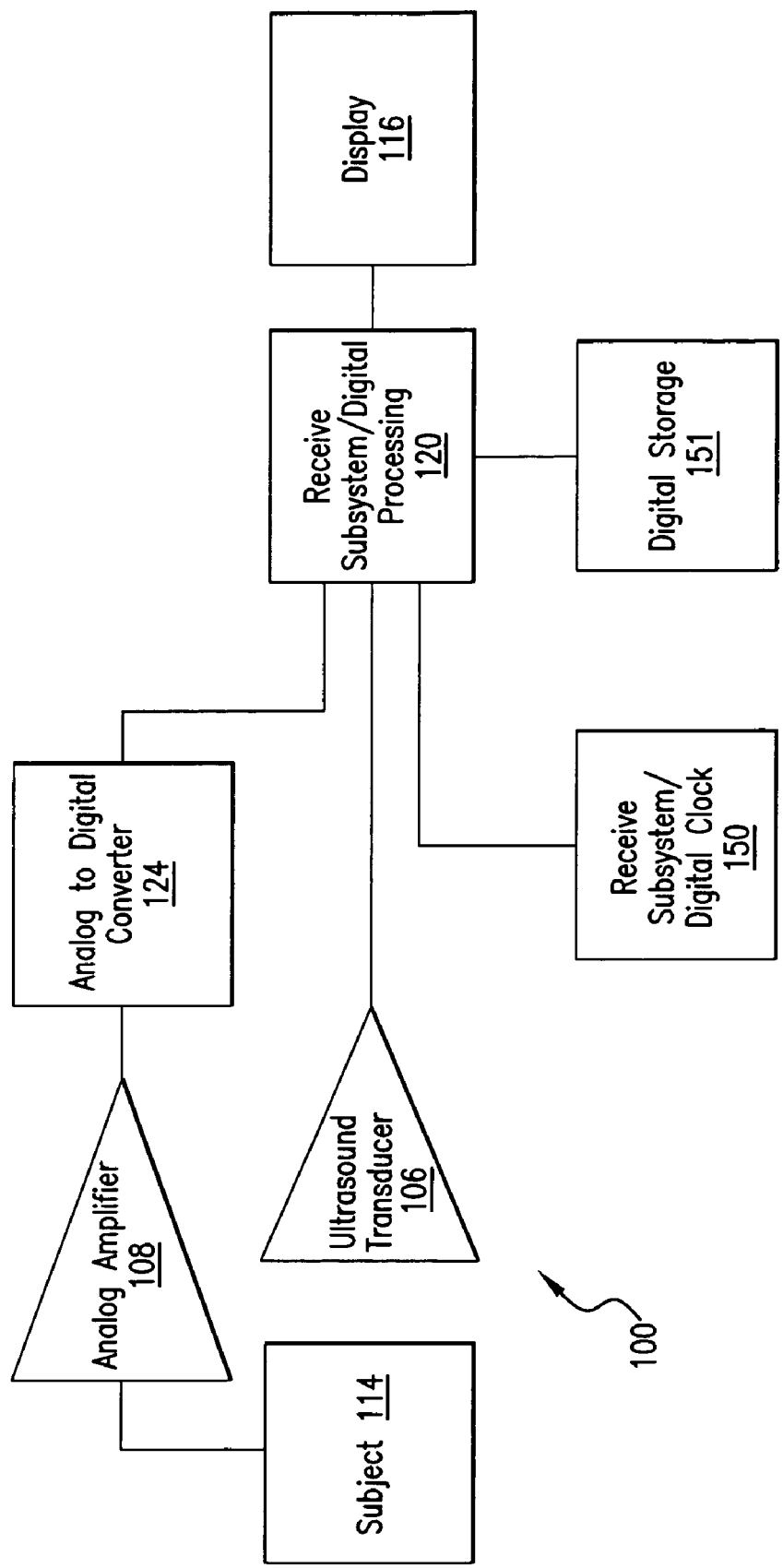
FIG. 1 is a block diagram illustrating an exemplary imaging system.

Provided herein are systems and methods for capture and synchronous display of blood pressure and ultrasound data. These methods and systems allow for accurate determination of pressure-volume or pressure-dimension relationships in the cardiovascular system of human patients and small animal subjects.

As used throughout, the singular forms "a," "an" and "the" include plural referents unless the context clearly dictates otherwise. Thus, for example, reference to "a processor" can include two or more such processors unless the context indicates otherwise.

By a "subject" is meant an individual. The term subject includes small or laboratory animals as well as primates, including humans. A laboratory animal includes, but is not limited to, a rodent such as a mouse or a rat. The term laboratory animal is also used interchangeably with animal, small animal, small laboratory animal, or subject, which includes mice, rats, cats, dogs, fish, rabbits, guinea pigs, rodents, etc. The term laboratory animal does not denote a particular age or sex. Thus, adult and newborn animals, as well as fetuses (including embryos), whether male or female, are included.

"Blood pressure" or "pressure" are used interchangeably herein and refer to the detectable pressure exerted by the circulating blood of a subject on the walls of the vessels or of the heart of the subject.

Provided herein is a method for the capture and display of ultrasound data and blood pressure data from a subject comprising capturing ultrasound data and blood pressure data from the subject. Optionally, the blood pressure and ultrasound data can be captured simultaneously from the subject. The captured ultrasound and blood pressure data can be timestamped, and the time-stamped data can be processed for display on a display device. Optionally, the time-stamped ultrasound data and the time-stamped blood pressure data are displayed synchronously on the display device.

"Synchronous display" or "displayed synchronously" means blood pressure and ultrasound data can be displayed simultaneously on a display device. The ultrasound data can also be displayed synchronously such that a time stamped B-mode frame or line of M-mode data can be displayed with a corresponding time stamped blood pressure data point. Such data can be considered to be in temporal synchrony. In one aspect, a processing system processes received ultrasound data signals to generate an ultrasound image and received blood pressure data signals to generate a blood pressure trace. The processing system can display the ultrasound image and blood pressure trace in a display image in which portions of the ultrasound image are displayed in temporal synchrony with portions of the blood pressure trace. For example, the processing system can be used to display an ultrasound image and a blood pressure trace in a display image in which portions of the ultrasound image having a given temporal identity are displayed with portions of the blood pressure trace having the same temporal identity.

Thus, portions of the ultrasound image can be displayed in temporal synchrony with portions of the blood pressure trace. A portion of the ultrasound image having a given temporal identity can be at least one line of ultrasound data signals. The at least one line can comprise an M-Mode ultrasound image. A portion of the ultrasound image having a given temporal identity can also be at least one frame of ultrasound data signals. For example, a frame of ultrasound data can comprise a B-Mode ultrasound image.

An ultrasound image or a portion thereof having a given temporal identity can be correlated with a blood pressure trace or a portion thereof having the same temporal identity. A plurality of ultrasound data signals and a plurality of blood pressure data signals can be correlated, each respective signal having a given temporal identity, by identifying respective data signals and pressure signals having the same temporal identities.

Capturing of echo signals or ultrasound data can comprise generating ultrasound, transmitting ultrasound into the subject, and receiving echos reflected by the subject. Received echoes can be used to produce an ultrasound image or portions thereof. A wide range of frequencies of ultrasound can be used to capture ultrasound data. For example, clinical frequency ultrasound (less than 20 MHz) or high frequency ultrasound (equal to or greater than 20 MHz) can be used. One of skill in the art can readily determine what frequency to use based on factors such as, for example, but not limited to, depth of imaging, or desired resolution.

High frequency ultrasound may be desired when high resolution imaging is desired and the structures to be imaged within the subject are not at too great a depth. Thus, capturing ultrasound data can comprise transmitting ultrasound having a frequency of at least 20 MHz into the subject and receiving a portion of the transmitted ultrasound that is reflected by the subject. For example, a transducer having a center frequency of about 20 MHz, 30 MHz, 40 MHz or higher can be used.

High frequency ultrasound transmission is often desirable for the imaging of small animals, where a high resolution may be achieved with an acceptable depth of penetration. The methods can therefore be used at clinical or high frequency on a small animal subject. Optionally, the small animal is selected from the group consisting of a mouse, rat, and rabbit.

Moreover, the methods and systems are not limited to any particular type of transducer. Any transducer capable of transmitting ultrasound at clinical or high frequency can be used. Many such transducers are known to those skilled in the art. For example, for high frequency transmission, transducers such as those used with the VisualSonics Inc. (Toronto, Calif.), Vevo®660 or Vevo®770 high frequency ultrasound systems can be used. High frequency and clinical frequency arrayed transducers and systems can also be used.

The ultrasound data can be captured as a line of ultrasound data or as a frame of ultrasound data. For example, a line of ultrasound can be captured in M-mode or a frame of ultrasound can be captured in B-mode. The captured ultrasound and blood pressure data can be time-stamped by using a digital clock. Optionally, the same digital clock can be used to time-stamp the captured ultrasound data and the blood pressure data. The ultrasound data can be displayed as an M-mode image or a B-mode frame or image and the pressure data can be displayed as a pressure waveform. Both the ultrasound data and the blood pressure data can be displayed on a display device.

The methods and systems can be used to image an organ located within a subject, or a portion thereof. Moreover, the organ, or portion thereof, can be imaged over time. For example, an M-mode image may comprise a two dimensional representation (depth and time) of an organ located within the subject, or a portion thereof, which can be produced from collected ultrasound data. M-mode imaging is a well known method to those of skill in the art. The image can also comprise a B-mode frame. One or more B-mode frames can be viewed in series to produce a loop of B-mode frames. B-mode imaging and the production of loops from B-mode frames are techniques known to those skilled in the art.

Many different organs of interest can be imaged including dynamic organs having a lumen. For example, a heart, or a portion thereof, can be imaged using the methods and systems described herein. The methods and systems are not limited to imaging the heart, however, and other organs, including other portions of the cardiovascular system can be imaged. Thus, for example, portions of the aorta can be imaged and analyzed.

Provided herein are methods that further comprise determining a dimension of an organ, or a portion thereof, at a point in time. The dimension can be determined by determining the distance between a first trace made on an M-mode image and a second trace made on the M-mode image, wherein the traces made correspond to at least one point in time.

A dimension of an organ or portion thereof at a point in time can be measured by measuring the distance between a first selected portion of an M-mode image having a temporal identity, and a second selected portion of the M-mode image having the same temporal identity, wherein the measured distance provides the dimension of the organ or portion thereof. The determined dimension at the point in time can be compared with a pressure reading taken at the same point in time to determine a pressure dimension relationship for that point in time. In one aspect, a further dimension of an organ or portion thereof at least at one subsequent point in time can be calculated from the distance between a first trace made on the M-mode image and a second trace made on the M-mode image, wherein the traces correspond to the at least one subsequent point in time.

Thus, a user can trace a structure located on an M-mode image using automated or semi-automated software. The user can also trace a second structure that is spaced some distance from the first tracing as viewed on the M-mode image display. The first and second trace are therefore separated by a distance (d). This distance may span a lumen, if an organ comprising a lumen is imaged. For example, if a portion of the heart is imaged, as is typical in M-mode echocardiography, a luminal wall of the heart is distinguishable from the lumen and from a corresponding luminal wall. Thus, a chamber of the heart, such as a ventricle can be imaged by M-mode ultrasound, which provides a cross sectional image wherein structures reflecting the transmitted ultrasound are displayed based on their distance from the transducer.

Figure 6:
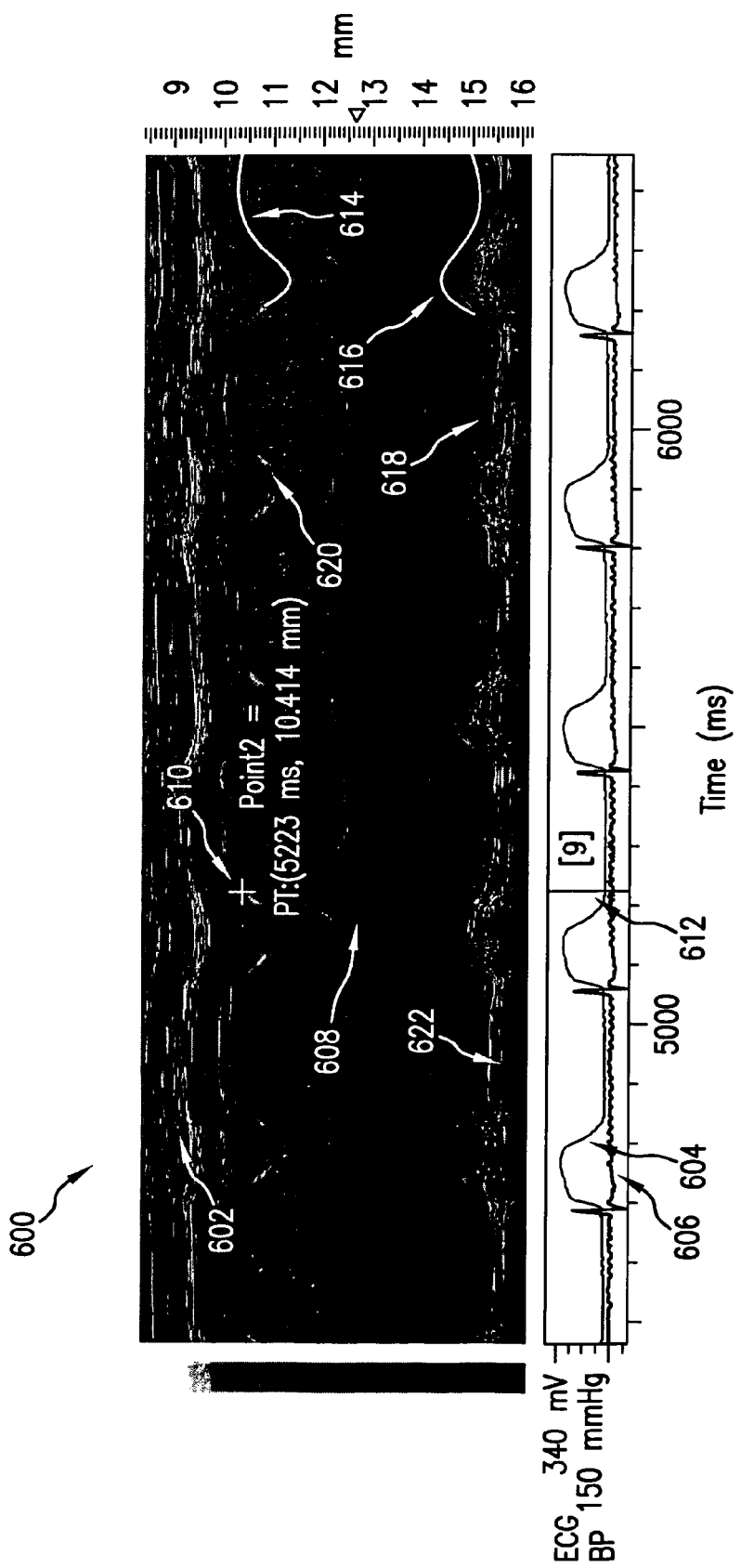
FIG. 6 is an image of an exemplary display of M-mode ultrasound data, blood pressure data, and ECG data produced using the exemplary system of FIG. 1 and FIG. 2.

As show in FIG. 6, an M-mode display shows a wall 602 of a heart chamber having a surface 620 overlying a lumen 608, and the lumen overlies a wall 622 of the heart having a second surface 618. As the M-mode image scrolls, one imaged portion of the heart is imaged dynamically over time and the contraction and relaxation of the heart walls can be visualized and/or the narrowing and expansion of the lumen can be visualized in real time at that anatomic cross section of the heart.

The disclosed methods can further comprise comparing the determined dimension of the organ, or portion thereof, at the point in time with a pressure reading taken at the same point in time to determine a pressure dimension relationship for that point in time. A dimension of the organ or portion thereof can be determined at least at one subsequent point in time by calculating the distance between a first trace made on the M-mode image and a second trace made on the M-mode image, wherein the traces correspond to the at least one subsequent point in time. The determined dimension at the at least one subsequent point in time can be compared with a pressure reading taken at the same point in time to determine a pressure dimension relationship for that point in time. Optionally, the pressure dimension relationship is a pressure to diameter relationship. Optionally, the pressure to diameter relationships are determined at a plurality of time points and are expressed as a pressure to dimension loop. Moreover, a volume of an imaged object can be determined from the M-mode image and a pressure to volume relationship can be determined. For example, in M-Mode the volume of an object or portion thereof, for example, a ventricle, can be estimated using the Teicholz formula:

$$v = \frac{7.0}{2.4 + d} \times d^3$$

Where:
v is the estimated volume in micro liters
d is the dimension in millimeters of the ventricle measured on the M-Mode image.

Figure 10:
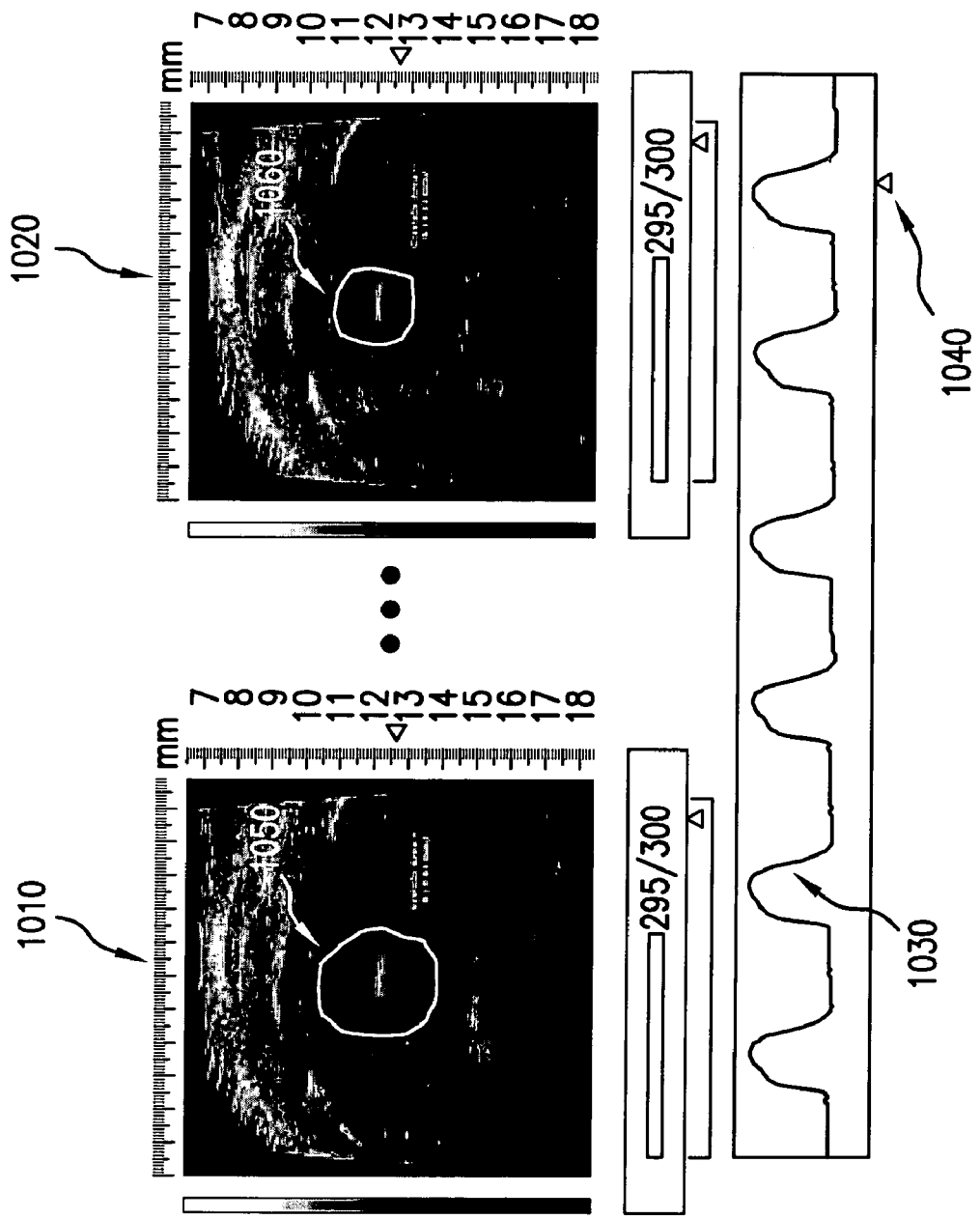
FIG. 10 is a schematic diagram illustrating two exemplary B-mode frames and an exemplary blood pressure waveform.
Figure 11:
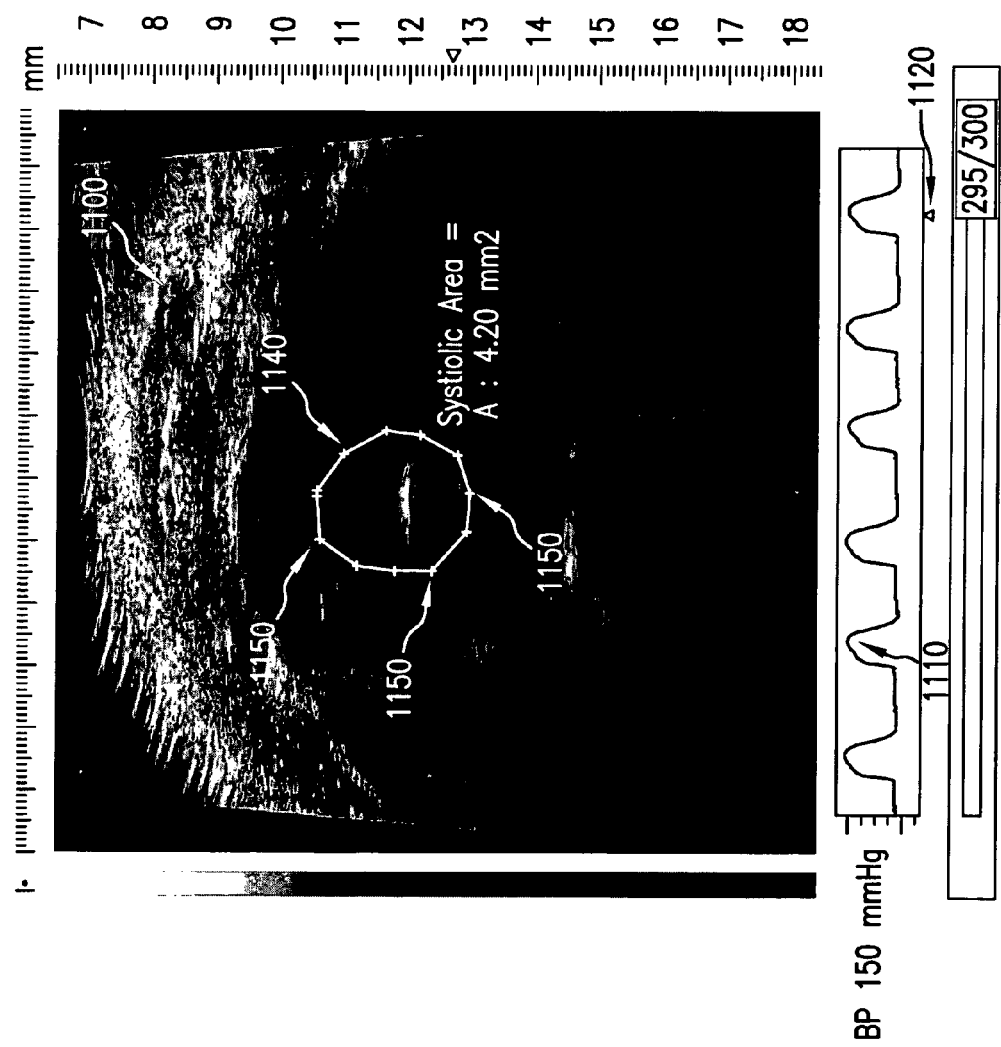
FIG. 11 is an image of an exemplary display comprising a B-mode frame and blood pressure data produced using the exemplary system of FIG. 1 and FIG. 2.

The methods described herein can also comprise determining an area or volume of an organ, or a portion thereof, at a point in time using one or more B-mode frames. The area and/or volume can be determined using a B-mode frame comprising an image of an organ or a portion thereof. For example, the imaged organ can comprise a lumen wherein the displayed B-mode frame or image is a cross sectional representation of the organ. Optionally, the organ is a heart. Exemplary B-mode frames comprising an image of a heart chamber are shown in FIG. 10 and FIG. 11.

A portion of the B-mode frame on the display device can be traced. The tracing can substantially follow a portion of the B-mode frame representing a luminal surface of the imaged organ to define an area. For example, the cross sectional shape of a chamber of a heart can be traced. Exemplary B-mode frames comprising an image of a heart chamber with a tracing substantially following the endocardium are shown in FIG. 10 and FIG. 11. Based on the traced area of the B-mode frame, the size of the area defined by the trace can also be determined. A volume corresponding to the area can be determined.

For example, in B-Mode the volume can be estimated using the Simpson's method. In this method, a long axis view of the ventricle is mathematically sliced as shown in the following diagram. The volume of each slice can be computed and then summed to produce the final volume. For example, the following equation can be used:

$$Vol = \sum_{i=1}^{n} \pi \times \left(\frac{d_i}{2}\right) \times h$$

Where:
v is the estimated volume in micro liters
d is the diameter in millimeters of each slice of the ventricle.
n is the number of slices
h is the spacing between the slices.

The determined volume can be compared with a blood pressure reading having the same time-stamp as the B-mode frame from which the volume was determined to determine a pressure volume relationship. Moreover, a volume can be determined from at least one subsequently displayed time-stamped B-mode frame and the volume determined from the subsequent frame can be compared with a pressure reading having the same time-stamp as the subsequent frame to determine a corresponding pressure volume relationship. The pressure volume relationship from a plurality of time points can be displayed as a pressure to volume loop.

A system for the capture and display of ultrasound data and blood pressure data from a subject comprises an ultrasonic transducer capable of transmitting ultrasound into the subject and of receiving reflected echo data or signals from the subject. The system can further comprise a blood pressure receiving mechanism or sensor capable of collecting blood pressure data from the subject and a processing system for receiving the reflected ultrasound data or echoes and the collected blood pressure data and for generating an image. The ultrasound data and the blood pressure data can be displayed synchronously on a display device. The transducer can be an array, a single element or another type of transducer. An array or non-array transducer can transmit clinical and/or high frequency ultrasound. Thus, the center frequency of the transducer may be at 20 MHz or higher or may be less than 20 MHz. The transducer can be a broadband transducer.

The processing system can be used or programmed for determining a pressure dimension relationship from the synchronously displayed ultrasound and blood pressure data. The processing system can comprise one or more processors. As one of skill in the art would recognize, where a single processor or processing system is described for performing multiple functions, multiple processors could be used for performing the same functions separately, and a combination of multi-functional and single function processors could also be used.

The processing system can be use or programmed for determining a dimension of the organ or portion thereof at a point in time by calculating the distance between a first trace made on an M-mode image and a second trace made on the M-mode image, wherein the traces comprise representative data from received echo data at one or more point in time. Moreover, the processing system can be used or programmed for comparing the determined dimension at the point in time with a pressure reading taken at the same point in time to determine a pressure dimension relationship for that point in time. The processing system can also be used or programmed for determining a dimension of the organ or portion thereof at least at one subsequent point in time by calculating the distance between a first trace made on an M-mode image and a second trace made on the M-mode image, wherein the traces comprise data representative of echo data corresponding to at least one subsequent point in time. The processing system can be used or programmed for comparing the determined dimension at the at least one subsequent point in time with a pressure reading taken at the same point in time to determine a pressure dimension relationship for that point in time. Optionally, the pressure dimension relationship is a pressure to diameter relationship. Optionally, the pressure to diameter relationships are determined at a plurality of time points and are expressed as a pressure to dimension loop.

The processing system can also be used or programmed for tracing a portion of a B-mode frame of an organ or portion thereof on a display device. If the organ comprises a lumen, for example a heart chamber, the tracing can substantially follow a portion of the frame representing a luminal surface of the imaged organ to define an area as shown in FIGS. 10 and 11. The processing system can be further used or programmed for determining the size of the defined area and for determining a volume corresponding to the defined area. The processing system can be further used or programmed for comparing the determined volume with a pressure reading having the same time-stamp as the B-mode frame from which the volume was determined to determine a pressure volume relationship. The processing system can be further used or programmed for determining a volume from at least one subsequently displayed time-stamped B-mode frame and comparing the volume determined from the subsequent frame with a pressure reading having the same time-stamp as the subsequent frame to determine a subsequent pressure volume relationship. The processing system can be used or programmed for expressing the pressure volume relationship from a plurality of time points as a pressure to volume loop.

Further provided herein is a system for the capture of ultrasound echo data and blood pressure data from a subject, comprising an ultrasonic transducer capable of transmitting ultrasound into the subject and of receiving reflected echo data from the subject. The system can further comprise a processing system for receiving the reflected echo data and for receiving blood pressure data collected from the subject.

Also provided herein is a system for the capture of echo data and blood pressure data from a subject, comprising a processor programmed for receiving echo data and for receiving blood pressure data collected from the subject.

FIG. 1 shows an exemplary ultrasound system 100 for the capture and display of blood pressure data with ultrasound image data. The ultrasound system 100 operates on a subject 114. The subject 114 can be a small animal, such as mouse, rabbit or rat, or the subject 114 can be a primate, such as a human.

A blood pressure signal can be obtained from the subject 114 using a blood pressure monitoring or detecting device. Such devices and methods are known in the art. For example, a Millar® catheter (Millar Instruments, Inc. Houston, Tex.), which converts blood pressure to an electric signal, can be used by inserting or positioning a catheter into the subject to acquire blood pressure data. The blood pressure data or signal from the subject can be converted into an analog waveform by the pressure detecting device.

Another example of pressure detecting device is a tail cuff. If the subject 114 is a small animal having a tail, a tail cuff may be placed around the tail and pressure data may be obtained using methods known to those skilled in the art. Furthermore, an implant may be used with an RF link that transmits blood pressure data from any point in the body. Thus, known methods and apparatuses for collecting blood pressure signals and for converting blood pressure signals into analog waveforms can be used in the ultrasound system 100. It is contemplated that any conventional device or method to collect a blood pressure signal from a subject and to convert it into an analog waveform can be used with the ultrasound system 100.

Figure 2:
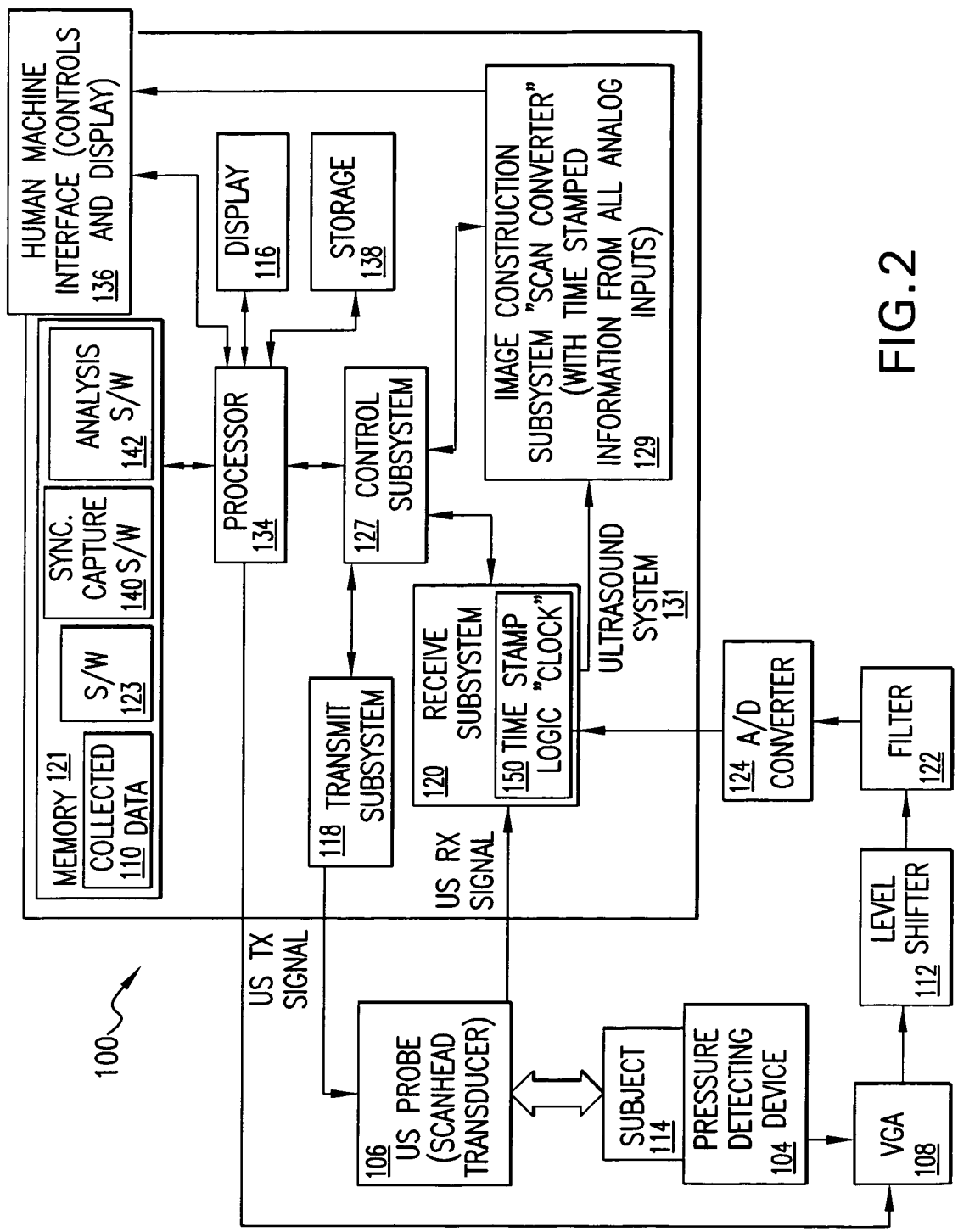
FIG. 2 is a block diagram further illustrating the exemplary imaging system of FIG. 1.

The analog waveform representing blood pressure data collected from the subject can be delivered into an analog amplifier 108. An exemplary analog amplifier is described in greater detail below. Analog pressure data can be processed and converted to digital data by an analog to digital converter 124 for provision to the ultrasound system 131, as shown in FIG. 2. The ultrasound system 131 is one example of a processing system that can be used. Digital data converted from analog data by the analog to digital converter 124 can be delivered to the receive subsystem 120 where digital processing occurs. Digital processing includes time-stamp logic or a time-stamp clock, which can be viewed as subcomponent 150 of the receive subsystem 120. Thus, the data from the analog to digital converter 124 can delivered to digital processing (see subsystem 150) and can be given a time stamp indicating a temporal characteristic of the data, i.e., the point of time at which that particular data was received by the receive subsystem of the ultrasound system.

In addition to the receipt of blood pressure data, the imaging system 100 collects ultrasound image data received by the ultrasound transducer 106, which can transmit and receive ultrasound of clinical or high frequency. Received echoes reflected from the subject or portions thereof, can be converted into an ultrasound receive signal that can be delivered to the receive subsystem 120. At block 120, the received ultrasound signal can be converted to digital data and can be time-stamped using the same time stamp logic 150 (FIG. 2) or clock that stamps the digital blood pressure data. Thus, at block 120, both blood pressure and ultrasound digital data are identified with a time stamp. Time-stamped data from the receive subsystem 120 can be stored in digital storage 151 which may include temporary storage in the random access memory 121 (FIG. 2) or on the hard drive 138 (FIG. 2) of the computer.

Image and blood pressure data can be displayed on a display 116. For example, image data can be displayed as an M-mode image as shown in FIG. 6 or as a B-mode frame as shown in FIG. 10 and FIG. 11. Pressure data can be matched and displayed synchronously with the M-mode image or B-mode frame. Thus, a synchronous display of an ultrasound image and a blood pressure waveform can be represented on the display.

Other sources of data can also be received from the subject 114, including ECG, respiration, and temperature data. These additional sources of data can be collected as analog data from the subject and converted to digital data by the analog to digital converter 124 for provision to the ultrasound system 131. This additional data can also be time-stamped at the receive subsystem 120 and can be displayed synchronously with a pressure waveform and M-mode or B-mode ultrasound image.

The synchronous display of the blood pressure data with the M-mode or B-mode ultrasound image allows for accurate pressure/dimension or pressure/volume measurements and/or estimations to be made. Moreover, the synchronous display with other received data from the subject, such as ECG data, allows concurrent analysis of pressure/dimension/volume with heart electrical activity or with the respiration cycle.

The blood pressure data can be matched and synchronously displayed with a corresponding vertical line of ultrasound data across the M-mode image or with a B-mode frame.

The M-mode image is like a strip recorder that flows from right to left at a given rate. The pressure data and, if used, the ECG data, and respiration data, can also continuously sweep right to left synchronously with the M-mode image. The M-mode image with the synchronously displayed pressure and/or ECG data can be frozen at any point in time allowing for any point along the M-mode image, any point along the pressure curve, or any point along the ECG display to be accurately matched on the display.

The system or method described herein can be used to analyze the cardiovascular system of the subject 114, including the beating of the heart or other pulsatile dynamics within the cardiovascular system, such as the dynamics of the aorta during systole and diastole.

The analysis of pressure data and dimension data from the image can be performed using software. In the example of the heart, the collected ultrasound data can be used to produce an M-mode image or a B-mode frame. In the M-mode image, two opposed waveforms (620 and 618) represent surfaces of the heart which contract and relax throughout the cardiac cycle. A B-mode frame comprises a depth and width dimension and can represent a cross sectional view of an imaged organ. For example, a cross sectional image of a heart can be imaged on a B-mode frame. The cross sectional image may include a lumen and luminal walls, which can be traced on the B-mode frame. The area and/or volume of a trace at a given cross section can be determined and can be correlated with a pressure reading having the same time stamp as the B-mode frame.

As described in greater detail below, any portion of the M-mode image or B-mode frame can be simultaneously or synchronously displayed with the corresponding pressure and/or ECG data such that a shift of the diameter of the ventricles, atria, or imaged portions thereof can be accurately compared with the pressure curve and/or ECG curve to allow simultaneous determination of pressure/dimension/volume relationships of the heart. Accurate determination of the pressure/dimension relationship and/or pressure/volume relationship of the heart can be used to produce pressure/dimension curves (loops) (FIG. 7) and/or pressure/volume curves (loops) (FIG. 12) that can be used to analyze physiological parameters of the heart.

FIG. 2 is a block diagram further illustrating the imaging system 100 of FIG. 1. The system 100 operates on a subject 114 and the ultrasound probe 106 can be placed in proximity to the subject 114 to obtain image information. As such, the ultrasound probe 106 can comprise a transducer for transmitting and receiving ultrasound to and from the subject, respectively. Such a transducer can comprise a single element transducer or an array, and can transmit and receive ultrasound at both clinical and high frequencies. Optionally, the center frequency of the transponder operates at or above 20 MHz.

The systems and methods for capture and display of blood pressure and ultrasound data can be implemented using a combination of hardware and software. The hardware implementation of the system can include any or a combination of the following technologies, which are all well known in the art, such as, discrete electronic components, a discrete logic circuit(s) having logic gates for implementing logic functions upon data signals, an application specific integrated circuit having appropriate logic gates, a programmable gate array(s) (PGA), a field programmable gate array (FPGA), and the like.

An exemplary imaging system 100 includes an ultrasound system 131. As described above, the ultrasound imaging system 131 described herein is an example of a processing system. The ultrasound system 131 can include a control system 127, a scan converter 129, a transmit subsystem 118, a receive subsystem 120, and a user input device 136. The processor 134 is coupled to the control subsystem 127, and the display 116 is coupled to a processor 134. The memory 121 is coupled to the processor 134. The memory 121 can be any type of computer memory and can be referred to as random access memory (RAM) in which software 123 and other software (140, 142) of the ultrasound imaging system executes. Other software may include capture software 140 and analysis software 142.

The software for the system can comprise an ordered listing of executable instructions for implementing logical functions, and can be embodied in any computer-readable medium for use by or in connection with an instruction execution system, apparatus, or device, such as a computer-based system, processor-containing system, or other system that can fetch the instructions from the instruction execution system, apparatus, or device and execute the instructions.

Memory 121 can also includes image data and pressure data (i.e., collected data 110) obtained by the imaging system 100. Collected data 110 can also include ECG data, respiration data and temperature data received by the ultrasound system. The processor 134 is coupled to the control subsystem 127 and the display 116 is coupled to the processor 134. A memory 121 is coupled to the processor 134. Software 123, 140, 142 controls the acquisition, processing and display of the ultrasound data and blood pressure data allowing the ultrasound system 131 to display an image including blood pressure data and may be used to determine pressure dimension or pressure volume relationships. Memory 121 can also include the collected data 110 obtained by the ultrasound system 131.

A computer readable storage medium 138 is coupled to the processor for providing instructions to the processor 134 to instruct and/or configure the processor 134 to perform steps or algorithms related to the operation of the ultrasound system 131. The computer readable medium can include hardware and/or software such as, by the way of example only, magnetic disk, magnetic tape, optically readable medium such as CD ROMs, and semiconductor memory such as PCMCIA cards. In each case, the medium can take the form of a portable item such as a small disk, floppy disk, cassette, or may take the form of a relatively large or immobile item such as a hard disk drive, solid state memory card, or RAM provided in the support system. It should be noted that the above listed example mediums can be used either alone or in combination.

In the context of this document, a "computer-readable medium" can be any means that can contain, store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium. More specific examples (a non-exhaustive list) of the computer-readable medium can include the following: an electrical connection (electronic) having one or more wires, a portable computer diskette (magnetic), a random access memory (RAM), a read-only memory (ROM), an erasable programmable read-only memory (EPROM or Flash memory) (magnetic), an optical fiber (optical), and a portable compact disc read-only memory (CDROM) (optical). Note that the computer-readable medium could even be paper or another suitable medium upon which the program is printed, as the program can be electronically captured, via for instance optical scanning of the paper or other medium, then compiled, interpreted or otherwise processed in a suitable manner if necessary, and then stored in a computer memory.

The control subsystem 127 is used to direct operation of various components to the ultrasound system 131. The control subsystem 127 and related components can be provided as software for instructing a general purpose processor or as specialized electronics in a hardware implementation.

The ultrasound system 131 includes a scan converter 129 for converting the electrical signals generated by the received ultrasound echoes to data that can be manipulated by the processor 134 and can be rendered into an image on the display 116. The control subsystem 127 is connected to a transmit subsystem 118 to provide an ultrasound transmit signal to the ultrasound probe 106. The ultrasound probe 106 in turn provides an ultrasound receive signal to the receive subsystem 120. The receive subsystem 120 also provides signals representative of receive signals to the scan converter 129. The receive subsystem 120 is also connected to the control subsystem 127. The scan converter 129 is directed by the control subsystem 127 to operate on the received data to render an image for display using the collected data 110. The collected data 110 can include, but is not limited to, the image data and blood pressure data. The receive subsystem 120 includes a subcomponent 150 which comprises time-stamp logic or a clock that can stamp received ultrasound signals from the ultrasound probe 106 with a temporal stamp identifying the data with a time identifier. The time identifier identifies data by the time it was collected from the subject 114 and/or when the data was delivered to or received by the receive subsystem 120. Pressure data and image data can be stamped by the same clock.

Figure 3:
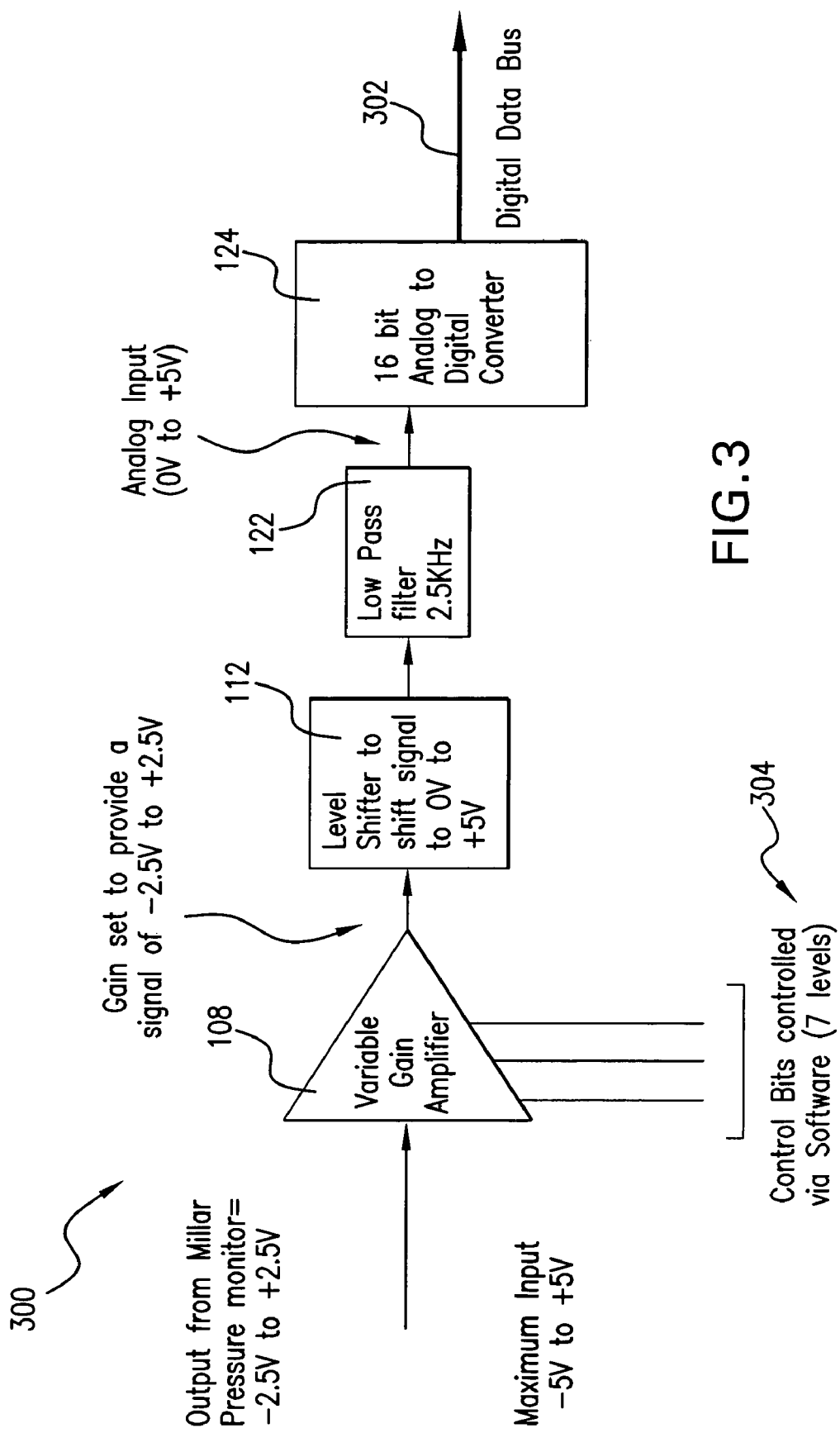
FIG. 3 is a schematic diagram illustrating portions of the exemplary imaging system of FIG. 1 and FIG. 2.

The imaging system 100 can further comprises a pressure detecting device 104 for obtaining blood pressure signals from the subject 114 and for converting the pressure signal received from the subject 114 into an analog waveform for delivery to a variable gain amplifier 108. As shown in FIG. 3, the variable gain amplifier can have seven levels of control and has three control bits. The gain can be controlled by the software 123 of the ultrasound system 131. The variable gain amplifier 108 allows for different input depending on the pressure detection device 104 used.

The imaging system 100 can further comprise a level shifter 112 which shifts the analog waveform from the variable gain amplifier 108 and delivers the shifted blood pressure data to a filter 122 which filters the data to remove data of a selected frequency. For example, a low pass filter can be used, for filtering data having a frequency at 2.5 KHz or greater. The amplified, shifted and filtered data can be delivered to an analog to digital converter 124 where it is converted from analog format to digital format. The digital data can be transmitted via a digital data bus to the receive subsystem 120 for digital processing including time stamping. The analog/digital converter 124 can also receive additional analog data from the subject 114 including ECG data, respiration data, and temperature data for provision along the digital data bus to the receive subsystem 120.

The ultrasound system 131 transmits and receives ultrasound data through the ultrasound probe 106, provides an interface to a user to control the operational parameters of the imaging system 100, and processes data appropriate to formulate still and moving images that represent anatomy and/or physiology which is presented to the user through the interface display 136 or display 116. Pressure and ultrasound data can be time-stamped for provision to the control subsystem and to the image construction subsystem, and for subsequent processing and/or storage and for synchronous display of pressure waves and M-mode or B-mode ultrasound image data on the display 116 and for subsequent pressure/dimension or pressure/volume analysis.

FIG. 3 is a schematic diagram illustrating portions of the exemplary imaging system 100 used to acquire and deliver pressure data from the subject 114 for the synchronous display and analysis with ultrasound M-mode or B-mode ultrasound data. Components shown in FIG. 3 include a variable gain amplifier 108, a level shifter 112, a low pass filter 122, an analog to digital converter 124, and a digital data bus 302.

The variable gain amplifier 108 includes three control bits which can be controlled via software 123 to seven levels. The variable gain amplifier 108 accepts input from the pressure monitoring/detecting device which can convert a pressure signal from the subject into an analog waveform. For example, if a Millar pressure monitor is used, the input into the VGA is typically in analog pressure waveform, varying from about −2.5 volts to +2.5 volts. Depending on the pressure monitor or detecting device used, however, the output, in terms of the analog pressure wave voltage, can vary. For example, if a tail cuff is used, the input into the variable gain amplifier can be in the form of an analog waveform with a swing from about −1.0 volts to +1.0 volts. One skilled in the art would appreciate that other swings of voltages are possible depending upon the input or pressure detecting device used and may be less than a swing of −1.0 to +1.0 volts or may be greater than a swing of −2.5 to 2.5 volts. For example, the variable gain amplifier 108 could accept input of −5.0 volts to +5.0 volts or greater.

The variable gain amplifier 108 allows the user to choose different voltage gains based on the input voltage swing of the analog waveform from the pressure detecting device. The gain of the variable gain amplifier can be set, depending on the input from the pressure-detecting device to provide a signal of −2.5 volts to +2.5 volts to the level shifter 112. Thus, if the input into the variable gain amplifier is an analog waveform with a −2.5 volts to +2.5 voltage swing, the gain would be 1. The variable gain amplifier 108 is controlled by three control bits to seven levels of control. The control bits 304 are controlled by software 123 to determine the gain of the variable gain amplifier 108 depending on the input from the pressure detecting device 104.

In one aspect, the level shifter converts or shifts the input voltage swing to a positive voltage swing. Thus, a swing of −2.5 volts to +2.5 volts is shifted to a positive voltage swing from 0 volts to +5.0 volts. The shifted signal is delivered to a low pass filter 122 which filters out portions of the signal with a frequency at 2.5 KHz or above. This filtering reduces out of band noise and also prevents the aliasing because the A/D converter typically runs at 8.0 KHz. The filtered analog signal is input into a 16 bit analog to digital converter 124 which converts analog input to the digital data output for provision to the ultrasound system 131 along a digital data bus 302.

Figure 4:
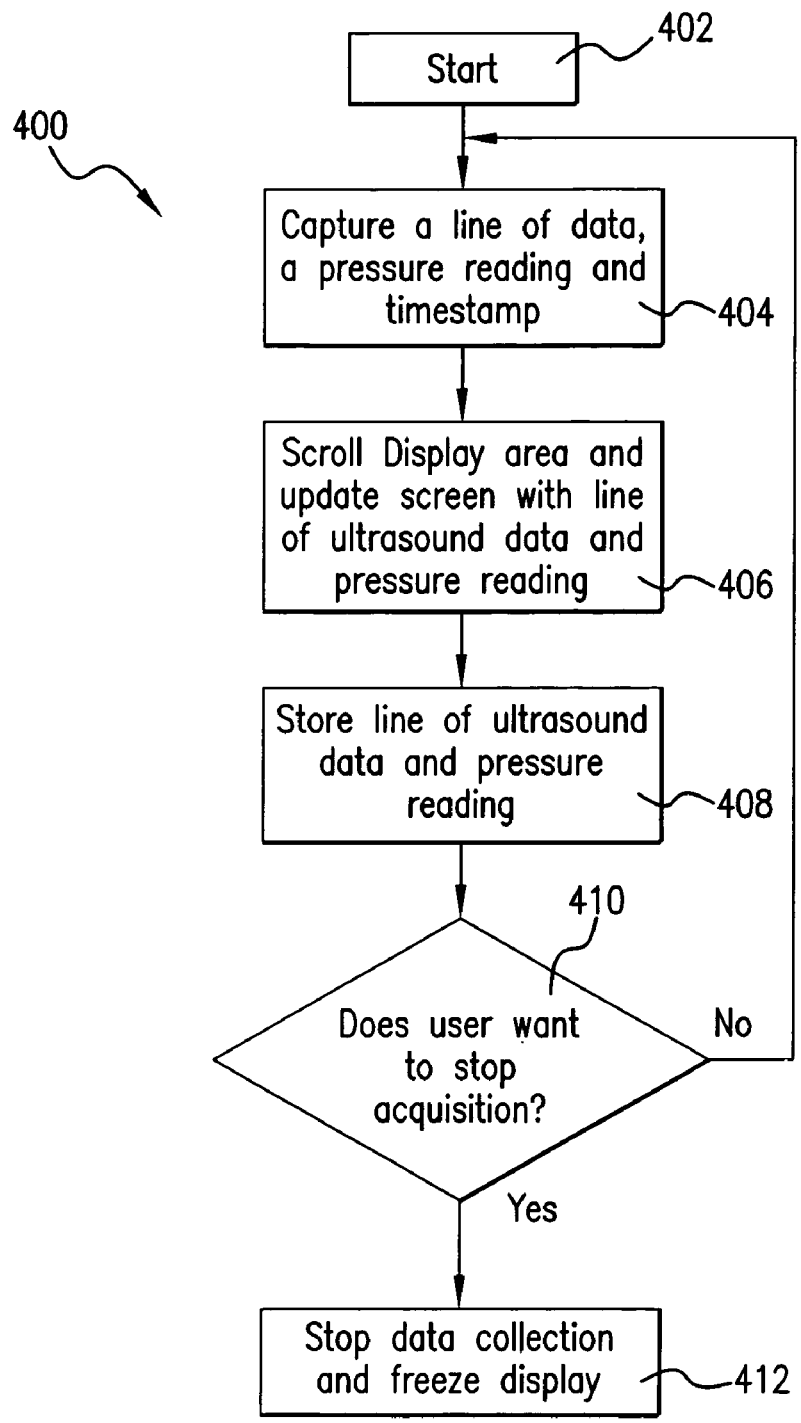
FIG. 4 is a block diagram illustrating an exemplary method for the capture and display of M-mode ultrasound data and blood pressure data using the exemplary system of FIG. 1 and FIG. 2.

FIG. 4 is a block diagram illustrating an exemplary method for the capture and display of M-mode ultrasound data or echo signals and blood pressure data using the exemplary system of FIG. 1 and FIG. 2. In general, ultrasound data can be captured as a series of lines at the same position of subject's anatomy over time. The captured lines of ultrasound data, along with captured pressure data can be time stamped and synchronously displayed. The pressure data can be displayed as a pressure waveform on a display device.

In block 402, an ultrasound probe comprising a transducer can be placed in proximity to a subject 114 to transmit ultrasound into the subject and to receive reflected ultrasound signals from the subject. A pressure detection device can be connected to the subject 114 through a lead or leads, allowing for the capture of pressure data and for the transformation of pressure data into an analog pressure wave.

In block 404, the imaging system 100 can capture a line of ultrasound data and captures a blood pressure reading. Optionally, the blood pressure and ultrasound data can be captured simultaneously from the subject. The captured line of ultrasound data and the captured blood pressure reading can be time-stamped by the ultrasound system 131 using the time stamp logic 150 of the receive subsystem 120. Synchronous lines of ultrasound data and pressure readings can be identified by having the same time-stamped identifier. In M-mode, a series of data lines can be captured at the same position of the anatomy over time. The line of data can be captured into a buffer. A captured line of ultrasound data can be displayed along with a captured pressure value reading. Because of the common time stamp on the ultrasound data line and the blood pressure reading, the data line and the pressure reading can be matched for synchronous real time display on the ultrasound system.

In block 406, as is typical to M-mode ultrasound, the display area can be scrolled and the display or screen can be updated with the line of ultrasound data and the pressure value reading captured in block 404. When the end of the screen is reached on the scroll, the oldest data falls off. As the oldest data falls off, the display can be updated with new lines of ultrasound data and pressure data until the user decides to stop the acquisition process at block 410.

In block 408, time-stamped ultrasound data and pressure data can be stored in RAM or on the hard drive of the computer for subsequent display or analysis. In block 410, the user can decide whether to stop acquisition process. If the answer is no, acquisition process can continue and one millisecond later, a second or new line of ultrasound data along with a second or new pressure reading can be captured at block 404. Again, the display can be updated with the oldest data falling of and the new ultrasound line and pressure data being updated onto the display as shown in block 406. The new data can be stored with previously stored data in block 408. The block of data stored in block 408 can be used for subsequent analysis in a rotating buffer which is filled as data is acquired. When the rotating buffer is full in 408, the next line of data can push the oldest line of data off of the rotating buffer.

If the user decides at block 410 to stop acquisition, data collection stops and the display can be frozen showing the M-mode image on the display of ultrasound system with a synchronous pressure waveform located on the M-mode image. FIG. 6 shows an exemplary display of ultrasound data and blood pressure data produced using the described method where the blood pressure data can be displayed synchronously with the M-mode image. At the end of the block diagram 400, the user has stopped acquisition and frozen the display in block 412. After the user has frozen the image in block 412, the stored data can be processed and analyzed as shown in FIG. 5.

Figure 5:
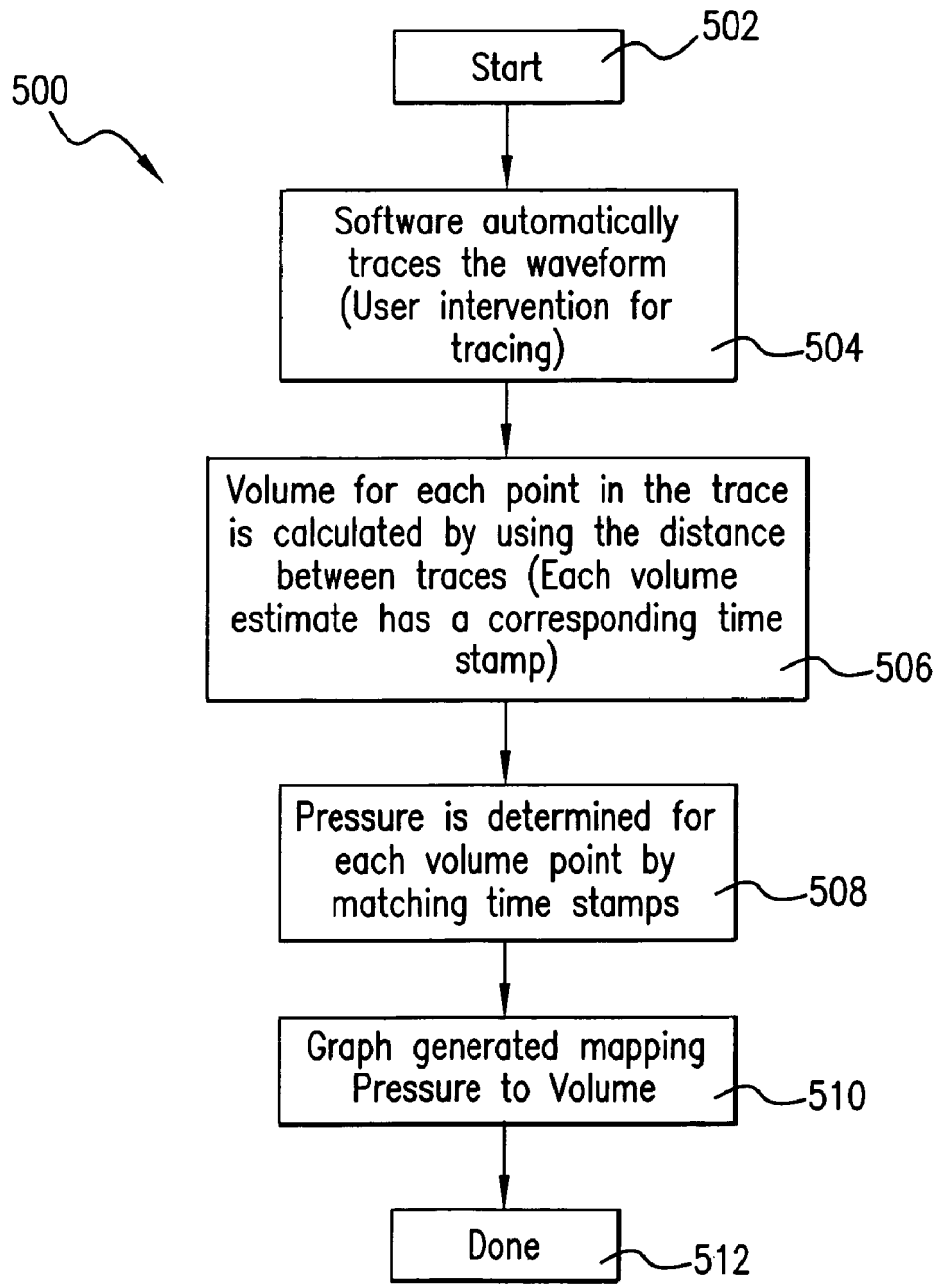
FIG. 5 is a block diagram illustrating an exemplary method of processing an M-mode ultrasound image and blood pressure data using the exemplary system of FIG. 1 and FIG. 2.

FIG. 5 is a block diagram illustrating an exemplary method of processing an M-mode ultrasound image using the exemplary system of FIG. 1 and FIG. 2. In block 504, a trace is laid onto the image that was frozen on the display in block 412. Two traces (614 and 616) can be created on the displayed image (FIG. 6). The analysis software 142 can be used to automatically trace both waveforms 620 and 618.

One tracing 614 traces the waveform 620 which is at approximately 10.5 mm in the exemplary image and the second tracing 616 traces the waveform 618 which is at approximately 15.0 mm in the exemplary image. Software 142 used to trace the waveform can be readily adapted using software for tracing waveforms known to those skilled in the art. Each point on a waveform (620 and 618) corresponds to a time-stamped line of ultrasound data acquired approximately 1 millisecond apart. Thus, each point along a trace (614 and 616) also corresponds to a time-stamped line of ultrasound data.

The distance (d) between the two traced waveforms or traces represents the dimension of imaged structure, for example, the diameter of the chamber of a heart at the location where ultrasound is being received. In block 506, a dimension, such as the diameter, volume or area, for each point in the trace can be calculated and/or estimated by using the distance between traces. Each calculated dimension or cross-section has a corresponding timestamp.

In block 508, pressure can be determined for each point on the pressure waveform and corresponding to a time point on a trace. Thus, the blood pressure from the pressure waveform can be determined for any dimension or volume point along the M-Mode image by matching timestamps along the pressure waveform with the identical time-stamp dimension determined by the two traces using the M-mode image. For example, assuming that the M-mode image is running at 1 KHz, every millisecond a line of data is acquired having a corresponding pressure and dimension. Thus, a new dimension or volume can be determined every millisecond. Readings can be determined quicker or slower than once every millisecond, however, depending on the speed of M-mode operation. For example, the speed may be 8 KHz. Thus, a sampling frequency can vary and can range, for example, from about 1 KHz to about 8 KHz. If the sampling rates are taken at 8 KHz, there are eight more readings per second than at 1 KHz. In one aspect, the pulse repetition frequency (PRF) in M-mode can be used for the sampling frequency.

In block 510, a graph can be generated using the pressure dimension or pressure volume data generated by the system. For example, a pressure volume or pressure dimension loop can be generated which allows analysis of stroke volume, cardiac output, and elasticity of the myocardium. A graph can also be produced that matches the pressure and dimension with ECG readings to determine volumes and pressures at different points of the cardiac cycle, including at the end of systole. Pressure dimension graphs can be produced using the data produced by the system because a single dimension is measured in M-mode. From the single dimension, an estimate of volume can be performed based on certain assumptions regarding the geometry of the heart.

FIG. 6 is an image of an exemplary display of ultrasound data, blood pressure data, and ECG data produced using the exemplary system of FIG. 1 and FIG. 2. FIG. 6 represents an exemplary M-mode ultrasound image 600 comprising multiple lines M-mode data displayed with and in synchrony with a pressure waveform 604 and an ECG trace 606. The M-mode looks across an axial line of data in real time and individual lines of data can be collected at a rate of 1 KHz. At 1 KHz, one line of data is acquired and captured every one millisecond.

During systole and diastole the walls of the heart 602 and 622 contract and relax such that the diameter of the heart chambers move dynamically throughout the heart cycle. As described above, the contraction and relaxation of the walls of the heart produce two waveforms (620 and 618) representing the distance of the heart walls (602 and 622) from the transducer when viewed in M-mode. These waveforms can be traced automatically by software which produce traces 614 and 616, wherein 614 traces a surface 620 of the heart closer to the transducer and 616 traces a surface 618 of the heart more distant from the transducer. For example, and as described above one waveform/trace is located at approximately 10.5 mm in depth and the other waveform/trace is located at approximately 15 mm in depth. The dimension or diameter of the lumen 608 of the imaged heart chamber, which is located in the space between the two surfaces (620 and 618), can be determined by measuring distance between the two traces at any point along the trace. Similarly, the pressure at any given point along the pressure trace 604 can be correlated with its synchronous point on a waveform of the heart surface by placing a cursor at a given point on the waveform, for example at point 610, wherein a corresponding line or other designating mark can be made along a pressure trace 604. For example, the linear mark 612 corresponds to the same point of identical timestamp as the cursor point 610, which is located along the waveform 620 of the wall 602. Also as shown in FIG. 6, the M-mode image and pressure waveform can be synchronized with an ECG trace 606, such that the pressure diameter and/or volume can be correlated synchronously with a given point in the electrical cycle of the heart.

Figure 7:
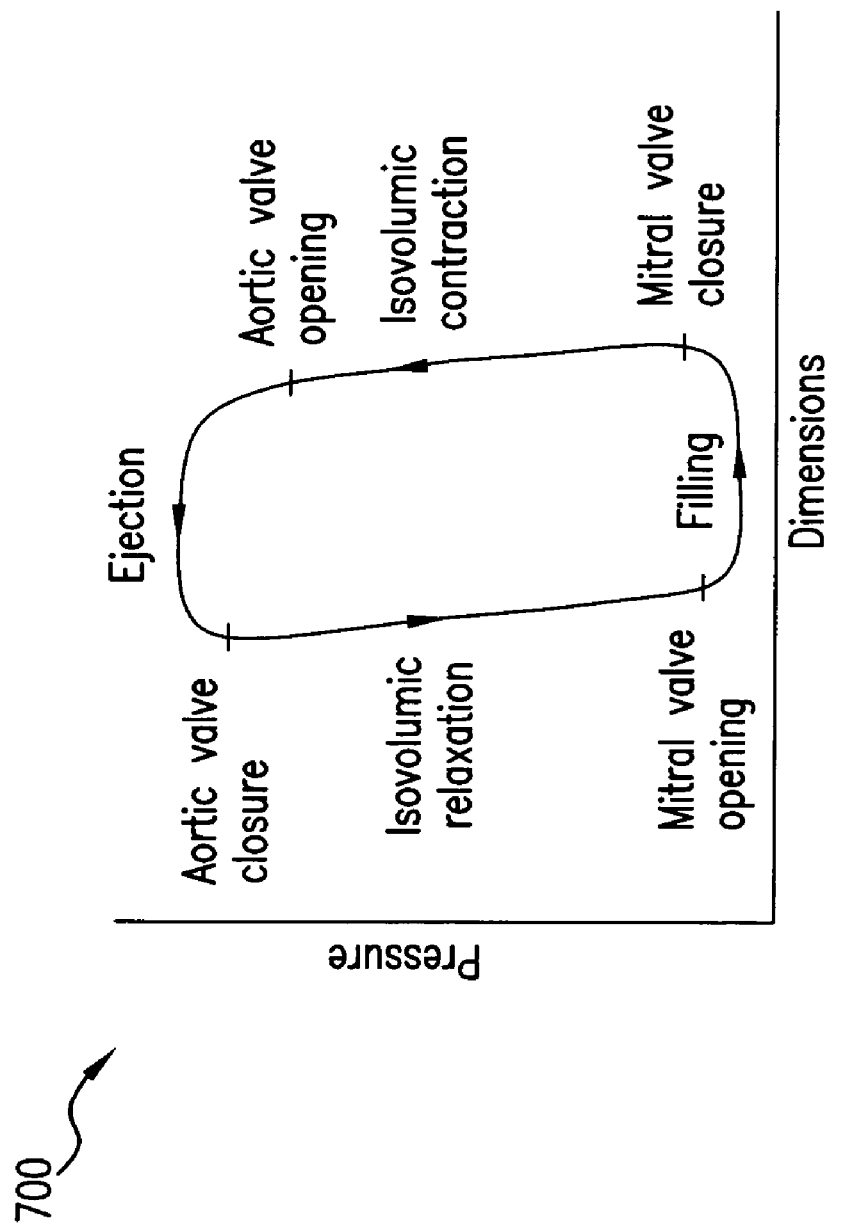
FIG. 7 is a schematic showing a pressure dimension loop graph and associated events in a typical cardiac cycle.

FIG. 7 is a schematic showing a pressure dimension loop graph and associated events in a typical cardiac cycle. Synchronous pressure/dimension or pressure/volume data can be attained by the display as shown in FIG. 6 using the methods described herein, and can be used to produce a graph relating dimension to pressure. Such a graph is called a pressure to dimension loop, an example of which is shown in FIG. 7. Through the pressure to dimension loop, the pressure within the chamber of the heart, as well as the dimension at the synchronous time of that pressure can be followed through the different phases of the heart cycle including the filling, mitral valve closure, isovolumetric contraction, aortic valve opening, ejection, aortic valve closure, isovolumeric relaxation, and mitral valve opening. Moreover, many parameters important to heart functioning can be determined by the pressure dimension graph which can be valuable for diagnosing cardiac disease or studying effects of therapeutics on cardiac function.

Figure 8:
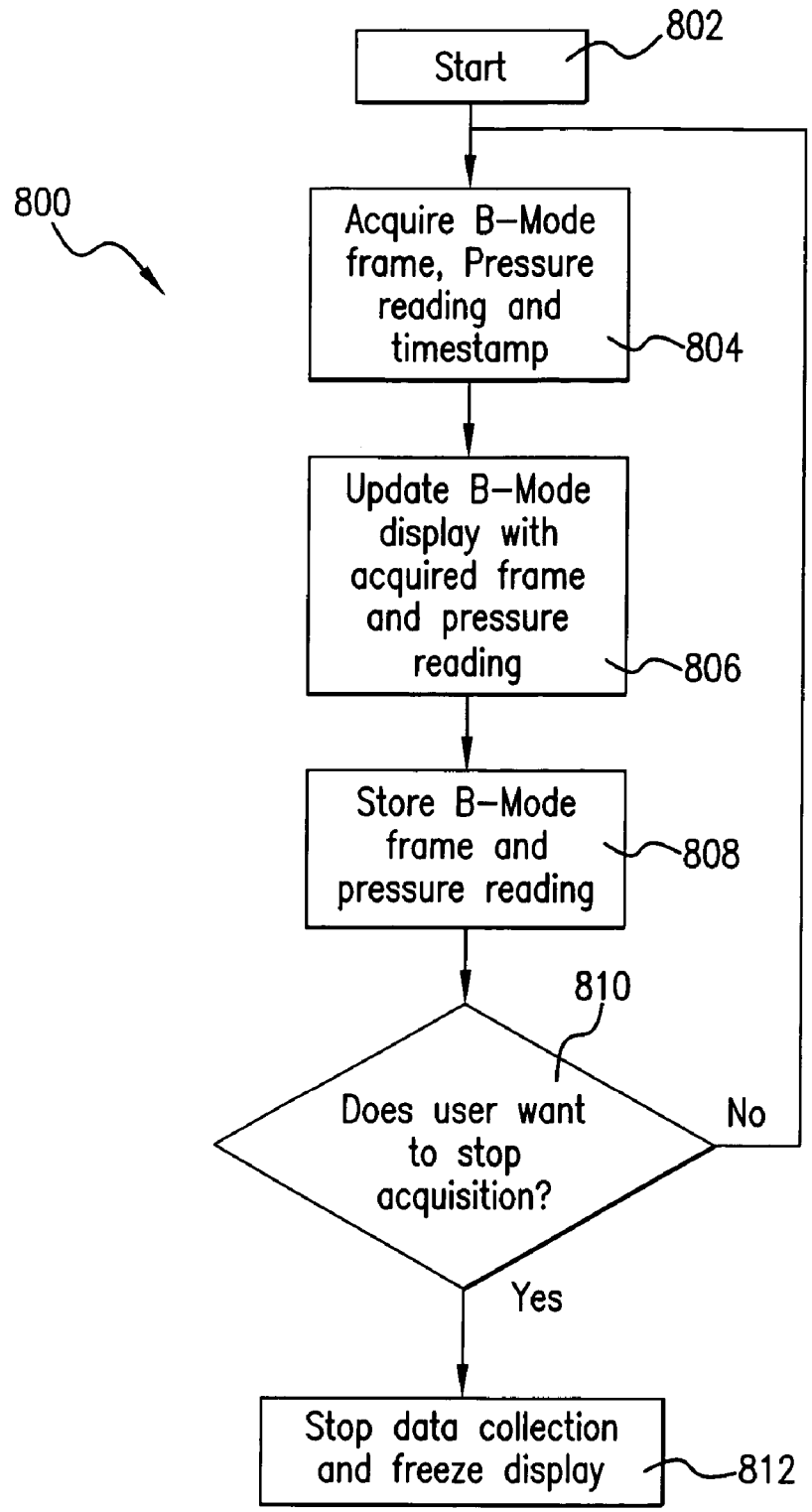
FIG. 8 is a block diagram illustrating an exemplary method for the capture and display of a B-mode frame or B-mode frames and blood pressure data using the exemplary system of FIG. 1 and FIG. 2.

FIG. 8 is a block diagram illustrating an exemplary method 800 for the capture and display of a B-mode frame or B-mode frames and blood pressure data using the exemplary system of FIG. 1 and FIG. 2. In Block 802, an ultrasound probe comprising a transducer can be placed in proximity to the subject 114 to transmit ultrasound into the subject 114 and to receive reflected echo signals or data from the subject. A pressure detection device 104 can be connected to the subject 114 through a lead or leads allowing for the capture of pressure data and for the transformation of pressure data into an analog pressure wave.

In Block 804, a frame of B-mode ultrasound can be acquired, and a pressure trace can be acquired using the methods and systems described above. Optionally, the blood pressure and ultrasound data can be captured simultaneously from the subject. During the time it takes to acquire a full B-mode frame, a plurality of blood pressure readings can be acquired by the system. In M-mode, for each line of acquired data there can be a corresponding acquired pressure data reading. For a frame of B-mode, there can be multiple pressure readings corresponding to the frame B-mode ultrasound data. One or more pressure reading can therefore be acquired per B-mode frame.

A B-mode frame can be acquired over a time period that can vary depending on the frame rate used to acquire the ultrasound data. The frame can vary from, for example, about 30 to about 230 frames per second (fps) and can be selected by the user depending on factors known to one skilled in the art. For example, a given frame rate can be selected based on heart rate, which can vary between the species imaged or other imaging conditions. Thus, for example, a frame rate allowing for the capture of at least about 5 to at least about 10 frames per heart cycle can be selected. Optionally, the selected frame rate is about 100 frames per second. Since the time for acquiring a B-mode frame time may vary depending on the frame rate, the number of pressure readings acquired during the time to acquire one B-mode frame can also vary.

The end of acquisition of the frame can be used as a time to give the frame a time stamp identifier. Any portion of the frame, however, including, but not limited to, the end of acquisition, the beginning of the acquisition, or any point there between, can be used as the time to time stamp an acquired frame.

Once a frame is acquired and time-stamped in Block 804, that frame can be drawn to the screen in Block 806. In block 806, the display can be updated with the frame acquired in Block 804 and with the pressure readings taken during the time in which the frame was taken in 804. Thus, the display in 806 can show a frame acquired in Block 804, along with a pressure waveform acquired during the time in which the frame was acquired in Block 804. FIG. 11 is an image of an exemplary display comprising a frame of B-mode ultrasound data 1100, and a pressure waveform 1110. The segment of the pressure waveform that corresponds to the time in which the frame was acquired can be displayed on the display with the acquired B-mode frame. An indicator 1120, which corresponds to the time stamp of the acquired frame 1100 can be placed on the pressure waveform 1110.

FIG. 10 is a schematic diagram illustrating two exemplary B-mode frames and an exemplary blood pressure waveform. FIG. 10 shows two B-mode frames 1010 and 1020 as would be displayed in Block 806. Each frame can be displayed independently or in a loop. When a loop is shown, a plurality of frames can be viewed in series to form a loop with each frame representing a frame of that loop. Thus, in FIG. 9, two exemplary frames of a loop are shown. The three dots between the frames schematically represent three additional frames taken between frame 1010 and 1020 that can be used to make up the loop. Two or more frames can be used to comprise a loop.

Below the two exemplary frames is an exemplary blood pressure waveform 1030. An indicator 1040 is superimposed onto the exemplary waveform 1030 to indicate the place in the waveform that corresponds to the timestamp of the current frame. "Current frame" means the frame that is currently being displayed on the display. However, each frame of a loop can have a separate time stamp, each with a corresponding time-stamped location on the pressure waveform.

In Block 808, a B-mode frame and the pressure readings can be stored and the system can check to see if the user is trying to stop acquisition at block 810. In Block 810, it can be determined whether to stop acquisition of ultrasound data and/or blood pressure data. If the user has tried to stop acquisition, then the display can be frozen and data collection can be stopped in Block 812. If the user has not tried to stop acquisition, another B-mode frame can be acquired along with a pressure reading, both of which can be time-stamped as described in Block 804, and the method can be repeated through the steps of the block diagram as described above.

Figure 9:
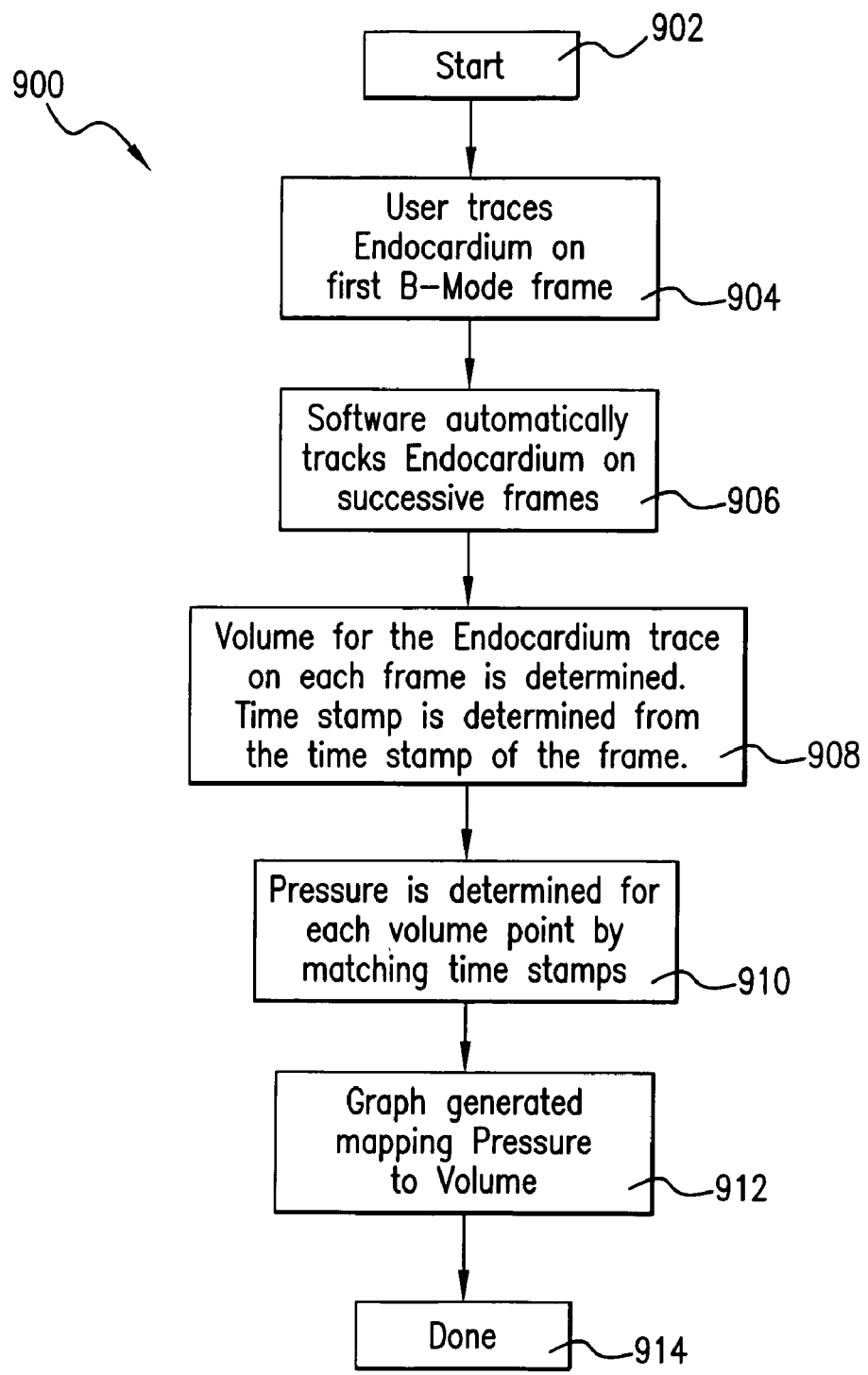
FIG. 9 is a block diagram illustrating an exemplary method of processing a B-mode frame or B-mode frames and blood pressure data using the exemplary system of FIG. 1 and FIG. 2.

Once a B-mode frame is frozen on the display with a corresponding pressure waveform, processing of the displayed image, including the B-mode frame and pressure trace, can be performed as shown in the exemplary method 900 as shown in FIG. 9.

FIG. 9 is a block diagram illustrating an exemplary method of processing a B-mode frame or B-mode frames and blood pressure data using the exemplary system of FIG. 1 and FIG. 2. In Block 904, a user traces the endocardium or other surface of the imaged organ, structured, or portion thereof, on the first or any B-mode frame acquired in Block 804. An exemplary tracing of endocardium on a B-mode frame that would be produced by a user in Block 804 is shown in FIG. 10 as 1050 on B-mode frame 1010 and by trace 1060 on B-mode frame 1020.

An exemplary tracing 1140 is also shown on an exemplary frame in FIG. 11. FIG. 11 is an image of an exemplary display of a B-mode frame and blood pressure data produced using the exemplary system of FIG. 1 and FIG. 2. Endocardium or another structure to be traced, such as a surface of any organ, the luminal surface of an organ comprising a cavity, or, for example, the inner surface of the aorta or a heart chamber can be traced manually by a user, working at the human machine interface 136. The user can draw an exemplary trace onto the display 116 by tracing manually the inner surface of the endocardium or other desired surface.

The surface can also be automatically traced using software 142, and once a trace is placed on a given frame, such as trace 1050 on frame 1010 of FIG. 10, then software 142 can automatically place a trace on each subsequent frame acquired, such as trace 1060 on frame 1020 of FIG. 10. Thus, a user may, in one example, trace a given structure and software 142 can automatically trace that structure through each subsequently acquired frame. Software used to trace the structure automatically between frames can be readily adapted using algorithms and software known to those skilled in the art. The process of tracing the structure can be automated or user-assisted automated. By user-assisted automated means that the user would place the first trace, for example, trace 1050 of FIG. 10 which is shown by a polygon traced by the user, and then the software would automatically place the trace 1060 on frame 1020 or any frame taken subsequent to frame 1020. The user can also adjust the traces automatically placed by the software to more closely follow the desired structure or, if automated software is not used, the user can manually place a trace on any frame taken from which the user desires to acquire data.

Automatic tracing by software on successive frames is shown in Block 906. The result of the processing that occurs in Block 906 is one of a series of B-mode ultrasound frames with a traced polygon or other geometric structure representing a surface of traced structure. The area can be calculated based on points of the polygon, examples of which are as shown in FIG. 11. In FIG. 11, multiple points 1150 are shown on the trace, which can be used to determine the area of the polygon using the software 142. The software can use algorithms known in the art.

Using other known formulas, the area can be converted into a volume reading or a volume estimate to determine the volume of the lumen of the organ or portion thereof that has been traced at that cross-section, or at the point where ultrasound has been transmitted and received for that particular B-mode frame. Thus, for example, the volume of a ventricle can be estimated by tracing the inner surface of the ventricle on the display, by determining the area within the traced geometry, and by converting the area using known formulas to a volume estimate of the ventricle.

The volume estimate can be based on the B-mode frame with a time stamp from which the volume estimate was produced. The pressure waveform can have a corresponding time stamp. Thus, as shown in 910, pressure can be determined for each volume by matching the time stamp of the frame or frames with the corresponding point of the blood pressure waveform.

Figure 12:
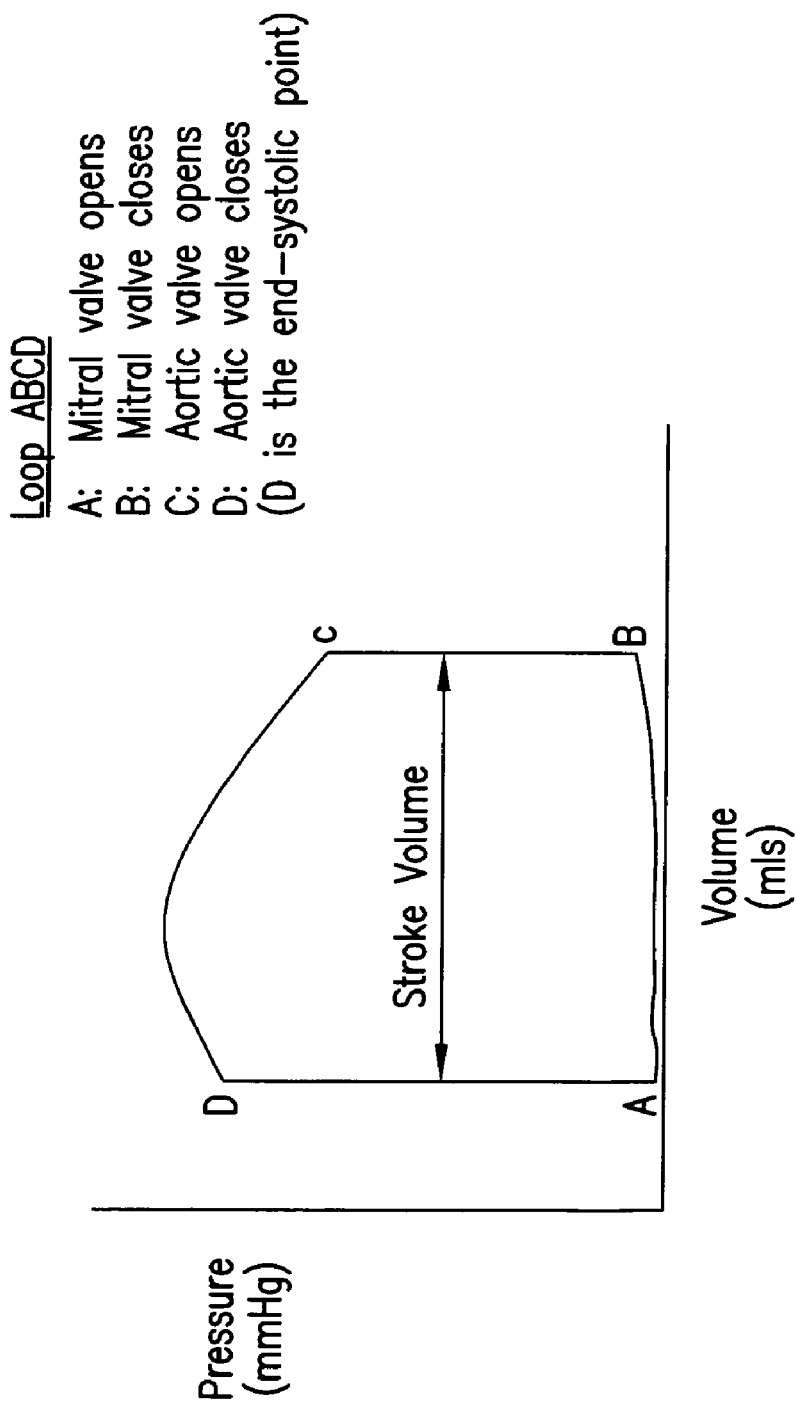
FIG. 12 is a schematic showing a pressure volume loop graph and associated events in a typical cardiac cycle.

In Bock 912, a graph, such as a pressure/volume graph can be produced similar to the pressure/dimension graph produced using the M-mode method. An exemplary pressure volume graph that can be produced is shown in FIG. 12. FIG. 12 is a schematic diagram showing a pressure volume loop graph and associated events in a typical cardiac cycle. The difference between M-mode and B-mode in this instance is that with M-mode, a dimension is acquired. The dimension in the M-mode graph is diameter. Whereas, in B-mode, an area can be acquired that can be converted to volume for a pressure to volume graph.

The foregoing detailed description has been given for understanding exemplary implementations of the invention only and no unnecessary limitations should be understood there from as modifications will be obvious to those skilled in the art without departing from the scope of the appended claims and their equivalents.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

What is claimed is:

1. A system, comprising:
   an ultrasound imaging probe configured to transmit ultrasound energy into a selected portion of a subject, to receive echoes therefrom, and to transmit ultrasound data signals representative thereof;
   a blood pressure sensor configured to measure a blood pressure of the subject and to transmit blood pressure data signals representative thereof; and
   a processing system including a clocking mechanism, wherein the processing system is operably connected to the ultrasound imaging probe and the blood pressure sensor, the clocking mechanism is configured to assign temporal identifiers to the respective ultrasound data signals and blood pressure data signals, the processing system is configured to generate a display that is dynamic by time and simultaneously includes representations of the ultrasound data signals and the blood pressure data signals corresponding to a plurality of temporal identifiers with portions of the representations of the ultrasound data signals and the blood pressure data signals visually associated according to each of the plurality of temporal identifiers.

2. The system of claim 1, wherein the representation of the ultrasound data signals includes an ultrasound image, the representation of the blood pressure data signals includes a blood pressure trace, and the processing system is configured to generate a display in which portions of the ultrasound image are displayed in temporal synchrony with portions of the blood pressure trace.

3. The system of claim 2, wherein the processing system is configured to correlate portions of the ultrasound image and portions of the blood pressure trace having the same temporal identity.

4. The system of claim 2, wherein a portion of the ultrasound image having a given temporal identity includes at least one line of the ultrasound data signals.

5. The system of claim 2, wherein a portion of the ultrasound image having a given temporal identity includes an M-mode ultrasound image.

6. The system of claim 2, wherein a portion of the ultrasound image having a given temporal identity includes at least one frame of the ultrasound data signals.

7. The system of claim 2, wherein a portion of the ultrasound image having a given temporal identity includes at least one B-mode ultrasound Image.

8. The system of claim 1, wherein the clocking mechanism is configured to assign the temporal identifiers to the ultrasound data signals and the blood pressure data signals by time of receipt from the subject.

9. The system of claim 1, wherein the clocking mechanism is configured to assign the temporal identifiers to the ultrasound data signals and the blood pressure data signals by time of receipt from the ultrasound imaging probe and the blood pressure sensor, respectively.

10. The system of claim 1, wherein the processing system is further configured to generate a dynamic representation of a calculated relationship between a dimension or volume based on the ultrasound data signals and a blood pressure based on the blood pressure data signals.

11. A method, comprising:
receiving ultrasound image data and blood pressure measurement data collected from a subject at a plurality of times;
identifying the received data with temporal identifiers; and
displaying a representation of the ultrasound image data and a representation of the blood pressure measurement data on a display such that portions of the representations of the ultrasound data signals and the blood pressure data signals corresponding to a plurality of temporal identifiers are displayed simultaneously and the portions of the representations of the ultrasound data signals and the blood pressure data signals are visually associated according to each of the plurality of temporal identifiers.

12. The method of claim 11, wherein the representation of the ultrasound image data includes an ultrasound image, the representation of the blood pressure measurement data includes a blood pressure trace, and portions of the ultrasound image are displayed in temporal synchrony with portions of the blood pressure trace.

13. The method of claim 12, further comprising correlating portions of the ultrasound image and portions of the blood pressure trace having the same temporal identity.

14. The method of claim 11, wherein a portion of the ultrasound image data having a given temporal identity includes at least one line of the ultrasound image data.

15. The method of claim 11, wherein a portion of the ultrasound image data having a given temporal identity includes an M-mode ultrasound image.

16. The method of claim 12, wherein the blood pressure trace includes a pressure waveform.

17. The method of claim 11, wherein a portion of the ultrasound image data having a given temporal identity includes a two-dimensional representation of an organ located within the subject or a portion of an organ located within the subject.

18. The method of claim 17, wherein the organ is a heart.

19. The method of claim 11, wherein a portion of the ultrasound image data having a given temporal identity includes at least one frame of the ultrasound image data.

20. The method of claim 11, wherein a portion of the ultrasound image data having a given temporal identity includes at least one B-mode ultrasound image.

21. The method of claim 20, wherein the representation of the ultrasound image data includes a B-mode frame and the representation of the blood pressure measurement data includes a pressure waveform.

22. The method of claim 21, wherein the B-mode frame includes an image of an organ or a portion thereof.

23. The method of claim 22, wherein the organ includes a lumen and the representation of the ultrasound image data includes a cross-sectional representation of the organ.

24. The method of claim 23, wherein the organ is a heart.

25. The method of claim 23, further comprising tracing a portion of the cross-sectional representation of the organ.

26. The method of claim 25, wherein tracing includes substantially following a portion of the cross-sectional representation of the organ, the portion representing a luminal surface of the organ, so as to define an area.

27. The method of claim 26, further comprising determining a size of the defined area.

28. The method of claim 26, further comprising determining a volume corresponding to the defined area.

29. The method of claim 28, further comprising comparing the determined volume with a pressure measurement having the same temporal identifier as the B-mode frame from which the volume was determined to determine a pressure-to-volume relationship.

30. The method of claim 29, further comprising determining a volume from at least one subsequently displayed B-mode frame and comparing the volume determined from the subsequent B-mode frame with a pressure measurement having the same temporal identifier as the subsequent B-mode frame to determine a corresponding pressure-to-volume relationship.

31. The method of claim 30, further comprising displaying the pressure-to-volume relationship from a plurality of times as a pressure-to-volume loop.

32. The method of claim 12, wherein the ultrasound image or a portion thereof having a given temporal identity can be correlated with the blood pressure trace or a portion thereof having the same temporal identity.

33. The method of claim 32, further comprising correlating a plurality of ultrasound image data points and a plurality of blood pressure measurement data points, each data point within either plurality having a given temporal identity, by identifying ultrasound image data points and blood pressure measurement data points having the same temporal identities.

34. The method of claim 33, further comprising producing a pressure-to-volume relationship from a plurality of the correlated ultrasound image data points and blood pressure measurement data points.

35. The method of claim 34, further comprising displaying the pressure-to-volume relationship as a pressure-to-volume loop curve.

36. The method of claim 11, wherein the received ultrasound image data and blood pressure measurement data is identified by its time of receipt from the subject.

37. The method of claim 11, wherein the received ultrasound image data and blood pressure measurement data is identified by its time of receipt from an ultrasound imaging probe and a blood pressure sensor, respectively.

38. The method of claim 11, further comprising:
calculating a pressure-to-dimension relationship, a pressure-to-volume relationship, or both based on the ultrasound image data and the blood pressure measurement data; and
displaying a dynamic representation of the pressure-to-dimension relationship, the pressure-to-volume relationship, or both.

* * * * *